United States Patent
Brocato et al.

(10) Patent No.: US 9,726,646 B1
(45) Date of Patent: Aug. 8, 2017

(54) RESONANT SURFACE ACOUSTIC WAVE CHEMICAL DETECTOR

(71) Applicant: National Technology & Engineering Solutions of Sandia, LLC, Albuquerque, NM (US)

(72) Inventors: Robert W. Brocato, Sandia Park, NM (US); Terisse Brocato, Sandia Park, NM (US); Larry G. Stotts, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 142 days.

(21) Appl. No.: 14/244,767

(22) Filed: Apr. 3, 2014

Related U.S. Application Data

(60) Provisional application No. 61/828,431, filed on May 29, 2013.

(51) Int. Cl.
*G01N 29/24* (2006.01)

(52) U.S. Cl.
CPC ... *G01N 29/2437* (2013.01); *G01N 2291/014* (2013.01); *G01N 2291/102* (2013.01)

(58) Field of Classification Search
CPC ......... G01N 29/2437; G01N 2291/014; G01N 2291/102; H03H 9/14505
USPC .................................. 73/579, 24.06; 310/313
See application file for complete search history.

(56) References Cited

U.S. PATENT DOCUMENTS

| 5,221,871 | A | * | 6/1993 | Fuchs | G01N 29/022 |
| | | | | | 310/313 R |
| 5,283,037 | A | * | 2/1994 | Baer | G01N 29/022 |
| | | | | | 310/311 |
| 5,306,978 | A | * | 4/1994 | Yamanouchi | H03H 9/14505 |
| | | | | | 310/313 B |
| 5,698,927 | A | * | 12/1997 | Tanaka | H03H 9/14505 |
| | | | | | 310/313 A |
| 5,977,846 | A | * | 11/1999 | Kajihara | H03H 9/14505 |
| | | | | | 310/313 B |

(Continued)

OTHER PUBLICATIONS

MacDonald, Dissertation: Experimental Investigation of Mass Sensing With Surface Acoustic Wave Devices, 2010.*
Smith, Thesis: Increasing the Sensitivity of Surface Acoustic Wave (SAW) Chemical Sensors and Other Chemical Sensing Investigations, 2010.*

(Continued)

*Primary Examiner* — David L Singer
(74) *Attorney, Agent, or Firm* — Martin I. Finston

(57) ABSTRACT

Apparatus for chemical detection includes a pair of interdigitated transducers (IDTs) formed on a piezoelectric substrate. The apparatus includes a layer of adsorptive material deposited on a surface of the piezoelectric substrate between the IDTs, where each IDT is conformed, and is dimensioned in relation to an operating frequency and an acoustic velocity of the piezoelectric substrate, so as to function as a single-phase uni-directional transducer (SPUDT) at the operating frequency. Additionally, the apparatus includes the pair of IDTs is spaced apart along a propagation axis and mutually aligned relative to said propagation axis so as to define an acoustic cavity that is resonant to surface acoustic waves (SAWs) at the operating frequency, where a distance between each IDT of the pair of IDTs ranges from 100 wavelength of the operating frequency to 400 wavelength of the operating frequency.

8 Claims, 4 Drawing Sheets

(56) References Cited

U.S. PATENT DOCUMENTS

| | | | | |
|---|---|---|---|---|
| 6,147,574 | A * | 11/2000 | Kidoh | H03H 9/14505 310/313 B |
| 6,194,809 | B1 * | 2/2001 | Takeuchi | H03H 9/0259 310/313 B |
| 6,255,759 | B1 * | 7/2001 | Takeuchi | H03H 9/6423 310/313 R |
| 6,285,112 | B1 * | 9/2001 | Takeuchi | H03H 9/0259 310/313 A |
| 6,373,353 | B1 * | 4/2002 | Takeuchi | H03H 9/02716 310/313 A |
| 7,047,792 | B1 * | 5/2006 | Bhethanabotla | G01N 29/022 73/24.01 |
| 7,075,390 | B1 * | 7/2006 | Bungo | H03H 9/14505 310/313 A |
| 7,878,063 | B1 * | 2/2011 | Cular | G01N 29/024 310/313 B |
| 2002/0171329 | A1 * | 11/2002 | Jian | H03H 9/14505 310/313 D |
| 2003/0122449 | A1 * | 7/2003 | Bergmann | H03H 9/02748 310/313 B |
| 2005/0099090 | A1 * | 5/2005 | Hartmann | H03H 9/02685 310/313 D |
| 2006/0132248 | A1 * | 6/2006 | Lichter | H03B 5/326 331/107 A |
| 2009/0085692 | A1 * | 4/2009 | Tsuda | H03H 9/14547 333/193 |
| 2009/0314062 | A1 * | 12/2009 | Tsuyoshi | F04B 17/003 73/53.01 |
| 2010/0102901 | A1 * | 4/2010 | Tsuda | H03H 9/02716 333/195 |
| 2010/0223999 | A1 * | 9/2010 | Onoe | H03H 3/08 73/579 |
| 2010/0236322 | A1 * | 9/2010 | Kogai | G01N 29/022 73/53.01 |
| 2012/0073390 | A1 * | 3/2012 | Zaghloul | G01N 29/022 73/865 |
| 2012/0105174 | A1 * | 5/2012 | Lee | H03H 9/6453 333/193 |
| 2013/0321103 | A1 * | 12/2013 | Elhakiki | H03H 9/0222 333/193 |
| 2015/0244348 | A1 * | 8/2015 | Damy | H03H 9/0222 333/195 |

OTHER PUBLICATIONS

Casalnuovo et al, Sandia Report: The Development of Integrated Chemical Microsensors in GaAs, 1999.*

Brocato et al., Optimized SAW Chemical Sensor with Microfluidic Packaging, May 29, 2012, 2012 IEEE 62nd Electronic Components and Technology Conference.*

Brocato et al., High Frequency SAW Correlator Module, 2003, IEEE 2003 Electronic Components and Technology Conference.*

Dickert et al, SAW devices-sensitivity enhancement in going from 80 MHz to 1 GHz, 1998, Sensors and Actuators B 46 (1998) 120-125.*

Campbell et al, Analysis and Design of Low-Loss SAW Filters Using Single-phase Unidirectional Transducers, 1987, IEEE Transactions on Ultrasonics. Ferroelectrics, and Frequency Control, vol. UFFC-34, No. 3, May 1987.*

Länge et al, Surface acoustic wave biosensors: a review, Feb. 12, 2008, Anal Bioanal Chem (2008) 391:1509-1519 DOI 10.1007/s00216-008-1911-5.*

Drafts, Acoustic/Ultrasound,Sensors Mag, Technology Tutorials Acoustic Wave Technology Sensors, Oct. 1, 2000, Sensors Online.*

Ferrari et al, Overview of Acoustic-Wave Microsensors, 2008, Piezoelectric Transducers and Applications, doi: 10.1007/978-3-540-77508-9_2.*

Frye, G.C. et al., "Optimizing Surface Acoustic Wave Sensors for Trace Chemical Detection," Intl. Conf. on Solid State Sensors and Actuators, Chicago, Jun. 16-19, 1997.

He, S., et al., "High Frequency Stability Oscillator for Surface Acoustic Wave Gas Sensor," Acoustic Sci. and Tech. vol. 30, No. 1, 2009, pp. 7-12.

Jasck, K., and Pasternak, M., "High Frequency SAW Stabilized Oscillators for Chemical Agents Sensors," Eur. Phys. J. Special Topics, vol. 154, 2008, pp. 97-102.

Urzednicozok, H., "Comparative Investigations of Two Kinds of Electronics Circuits for Multichannel SAW-based Gas Sensors," XIX IMEKO World Congress Fundamental and Applied Metrology, Sep. 6-11, 2009, pp. 2247-2251.

Wang, W., et al., "High Frequency Stability Oscillator for Surface Acoustic Wave-base Gas Sensor," Smart Mater. Struct., vol. 15, 2006, pp. 1525-1530.

Yoo, B.K., et al., "Surface Acoustic Wave Sensors to Detect Volatile Gases by Measuring Output Phase Shift," J. Electroceram, vol. 17, 2006, pp. 1013-1017.

* cited by examiner

Basic Surface Acoustic Wave Filter

DKAP

Phase Comparison Architecture for SAW-based Chemical Detection.

RESONANT SURFACE ACOUSTIC WAVE CHEMICAL DETECTOR

CROSS-REFERENCE TO RELATED APPLICATIONS

This application claims priority from U.S. Provisional Patent Application Ser. No. 61/828,431, filed May 29, 2013, and incorporated herein by reference.

STATEMENT OF GOVERNMENT INTEREST

This invention was developed under Contract DE-AC04-94AL85000 between Sandia Corporation and the U.S. Department of Energy. The U.S. Government has certain rights in this invention.

FIELD OF THE INVENTION

This invention relates to chemical detectors of the kind in which an analyte is detected by its effect on the propagation of a surface acoustic wave.

ART BACKGROUND

Chemical sensors based on surface acoustic wave (SAW) filters are known. A typical SAW filter consists of two interlaced comb-like metal structures, referred to as interdigitated transducers (IDTs), which are deposited on a piezoelectric crystal surface. The first IDT serves as a transducer to convert long wavelength radio waves to very short wavelength acoustic waves. The second IDT converts the acoustic waves back into an electromagnetic signal. By way of example, 3 GHz radio waves propagating in free space have wavelengths of 10 cm, whereas 3 GHz acoustic waves propagating in Y-Z lithium niobate, an illustrative piezoelectric material, have wavelengths of only 0.000116 cm.

Electrically, a SAW filter behaves as a band-pass filter. That is, it has very low insertion loss in a portion of the frequency spectrum (i.e. the pass band), and it has very high insertion loss in another portion of the spectrum (i.e. the stop band).

In operation, an alternating voltage, typically at microwave frequency, is applied across the first, transmitting, IDT. Because the substrate is piezoelectric, the applied voltage induces a mechanical distortion on the surface of the piezoelectric material which propagates preferentially along the surface of the crystal as an acoustic wave. Proper orientation of the underlying substrate can enable this wave to propagate as a surface-confined Rayleigh wave with little loss or dispersion. The addition of the second, receiving, second IDT creates a two-port electrical device which can be designed to respond electrically with the desired band pass configuration.

As is well-known in the art, confinement of the Rayleigh wave's energy into the thin surface region of the SAW device enables the creation of a sensitive mass detector. The basic principle of operation of such a detector is that mass loading due to chemical species adsorbed typically into the chemical coating on the substrate surface in the acoustic propagation path will cause a measurable change the propagation characteristics of the acoustic wave, typically observable as a phase delay, relative to a similar wave in a pristine reference device.

Accordingly, a measurement system will typically include two SAWs, i.e. a measurement and a reference device. These devices are substantially identical SAWs kept in close physical proximity under substantially identical conditions of temperature and exposure to the gas being measured. Both of these SAWs must be designed in a manner to provide a physical separation region between the two IDTs. The shape and size of this space between the IDTs along with the dimensions of the IDTs themselves largely determines the physical dimensions of the SAW. Additionally, the separation length between the IDTs affects the magnitude of the measurable phase delay and the insertion loss of the entire SAW. The width of the propagation path, which we refer to herein as the "aperture", is equal to the width of the IDTs.

For detection, an analyte is exemplarily injected into a stream of carrier gas, which then passes over the detector surface. For environmental sensing, a sample of the ambient atmosphere which may contain an analyte of interest may likewise be directed over the detector surface.

Although in some cases the bare substrate surface may adsorb sufficient analyte molecules to provide a measurable signal, it is more common to increase sensitivity by applying a sensitizing chemical coating to the surface of the substrate in the propagation path between the IDTs. A coating may be used that is an effective adsorbant for a general variety of chemical species, or a chemically selective adsorbant may be used. In the following discussion and claims, we will use the term "adsorbant" to refer to the sensitizing layer because adsorption is the most common mechanism for the retention of analyte molecules. However, we do not mean to exclude other possible sorption mechanisms such as absorption and chemisorption. Hence, the terms "adsorption", "adsorbant", and "adsorptive" should be understood broadly as encompassing all forms and mechanisms of sorption.

SAW-based chemical detectors have proven to be useful for numerous applications. However, there remains a need for detectors of still greater sensitivity.

SUMMARY OF THE INVENTION

We have invented such a detector. In an embodiment, we have provided an apparatus for chemical detection in which a pair of interdigitated transducers (IDTs) is formed on a piezoelectric substrate, and a layer of adsorptive material is deposited on a surface of the substrate between the IDTs. Each IDT is conformed, and is dimensioned in relation to an operating frequency and an acoustic velocity of the piezoelectric substrate, so as to function as a single-phase unidirectional transducer (SPUDT) at the operating frequency. The pair of IDTs is spaced apart along a propagation axis and mutually aligned relative to said axis so as to define an acoustic cavity that is resonant to surface acoustic waves (SAWs) at the operating frequency.

In embodiments, each IDT is conformed as a floating electrode uni-directional transducer (FEUDT). In embodiments, the FEUDT conformation of each IDT includes a pattern of one or more repeat units, each repeat unit comprises a plurality of metal strips, herein denominated fingers, that project substantially perpendicularly to the propagation axis; and each repeat unit comprises two driver fingers that are electrically connected to opposite signal-carrying conductors, two floating fingers that are individually electrically floating; and two shorted fingers that are electrically shorted to each other.

In embodiments, each IDT comprises a plurality of metal strips formed on a surface of the piezoelectric substrate and extending substantially perpendicularly to the propagation axis. We refer to such strips as "fingers". The fingers form a repeating pattern along the propagation axis. A further plurality of fingers, which we refer to as "velocity-correcting fingers", are formed in a repeating pattern along the propagation axis on at least a portion of the substrate that lies between the IDTs.

In embodiments, the apparatus comprises at least one measurement sensor, at least one reference sensor, and an electronic circuit connected to the measurement and reference sensors. The measurement sensor includes an IDT pair and adsorptive layer as described above. The reference sensor also includes an IDT pair as described above. The electronic circuit is conformed to detect phase differences between respective signals transmitted across the measurement and reference sensors. In embodiments, the electronic circuit includes a precision oscillator, such as an oven-controlled oscillator, connected to a transmitting IDT of each pair so as to drive acoustic oscillations of the transmitting IDTs, the electronic circuit includes a phase detector that is connected to a receiving IDT of each pair and conformed to provide an output signal that is indicative of the phase differences described above, and the electronic circuit further comprises a matched filter connected to the output of the phase detector. The matched filter is conformed to reject low-frequency drift components and high-frequency noise from the phase-detector output and is timeable to match expected responses in the phase-detector output.

DETAILED DESCRIPTION

Figure 1:
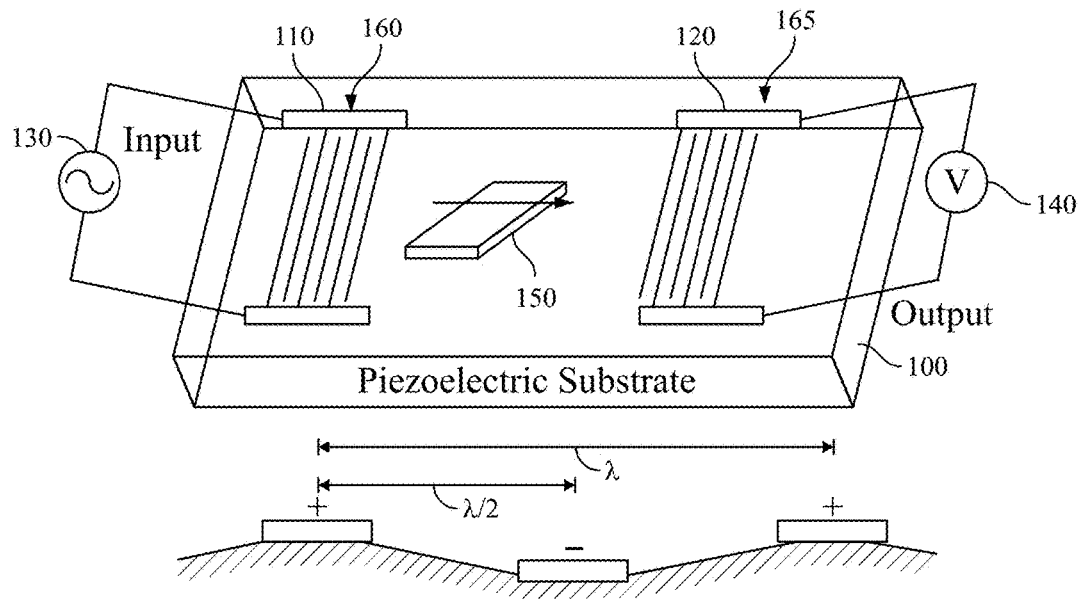
FIG. 1 provides a partially schematic, perspective view of a typical SAW chemical detector of the prior art.

As seen in FIG. 1, a typical SAW device includes piezoelectric substrate 100, transmitting IDT 110, and receiving IDT 120. In operation, source 130 of an oscillating voltage is applied across IDT 110, and receiver circuit 140 detects the voltage response of IDT 120 to the received acoustic wave. For use in a chemical detector, a layer 150 of sensitizing coating material is deposited on the substrate surface in the propagation path between the IDTs.

With further reference to FIG. 1, it will be seen that each IDT includes an upper (as seen in the figure) bus bar 160 and a lower bus bar 165. Electrically connected to the upper bus bar are a plurality of downwardly (as seen in the figure) extending projections, or "fingers", and there are likewise a plurality of fingers extending upwardly from the lower bus bar. Each upwardly extending finger, together with an adjacent downwardly extending finger, constitutes a repeating unit that we refer to herein as a "finger pair". Reference to the figure will show that in the particular example illustrated here, each of the IDTs contains three finger pairs.

In a comparative arrangement for chemical sensing, layer 150 is typically applied to the measurement SAW device, but not to the reference device. In such a case, layer 150 will unbalance the insertion losses of the respective devices to some degree. For that reason, the coating is desirably made thin enough to maintain an insertion loss degradation of no more than about 3 dB. If the insertion loss difference between the two SAWs is imbalanced by more than this, then an attenuator is desirably used on the output of the reference SAW to bring its insertion loss into line with that of the measurement device.

Two exemplary piezoelectric materials suitable for substrate materials in a SAW device are lithium niobate and quartz. For example, the illustrative embodiment of our invention to be described below is fabricated on a substrate of Y-propagation, Z-cut lithium niobate. Titanium nitride, deposited e.g. on sapphire, is a further piezoelectric material that may be of similar interest.

SAW filters structures are generally fabricated using industry-standard processing methods. The SAW devices may be produced, e.g., using a two-step lithographic process wherein the IDTs are patterned in a first step, followed by a metal bond pad layer that is patterned in a second step.

In an exemplary fabrication process, the IDT layer metal is composed of 500 Å of aluminum deposited onto the surface of the piezoelectric substrate. This metal layer is kept thin to prevent acoustic reflections from occurring in the IDTs. The second metal layer consists of 5000 Å of gold and is added to provide mechanical bond strength and good conductivity of RF signals from bond pads to the IDTs. Contact optical photolithography patterning methods are advantageously employed wherever possible. However, devices designed to operate at frequencies above approximately 800 MHz are so finely scaled that electron-beam lithography is at present the optimum method for patterning the fingers, i.e., the interlaced protrusions of the IDT patterns. The electron beam lithography step, if needed, is followed by an optical lithography step to define the bond pad layer. An alignment structure is desirably included in the layout to correctly align the layers during processing.

The starting substrate material in our exemplary process is a 100 mm diameter, circular, Y-Z cut lithium niobate wafer with an acoustic velocity of 3488 m/s. The wafers used are flat to electronic-grade tolerance. An organic solvent rinse is used to remove residues from the wafers that may accumulate during shipping.

The IDT layer is patterned on the substrate using a standard liftoff process. That is, the aluminum for the IDT layer is deposited on top of exposed photoresist, which is then selectively removed to leave an aluminum pattern. Following the IDT layer, the wafers undergo both solvent and oxygen plasma cleaning processes to remove organic residues. The metal bond pad layer is then patterned on the wafer.

The lithography of the metal bond pad layer is a routine liftoff process that we have modified to protect the aluminum metallization from etching by the photoresist developers. First, a blanket layer of silicon nitride is deposited over the entire wafer, and a metal2 (gold-on-chromium) layer for the bond pads is patterned over the top of the silicon nitride. The open areas of the gold are then processed using dry plasma etch through the silicon nitride to expose the aluminum IDT metal. The plasma silicon nitride etch process does not etch the aluminum bus-bars as the liquid photoresist does, and the bus-bars remain exposed. The 5000 Å thick gold layer is then deposited with an underlying 150 Å thick chromium adhesion layer. This leaves the bond pad metal fully patterned. Finally, following liftoff of the gold layer, a blanket-etch of the silicon nitride exposes the entire wafer.

Figure 2:
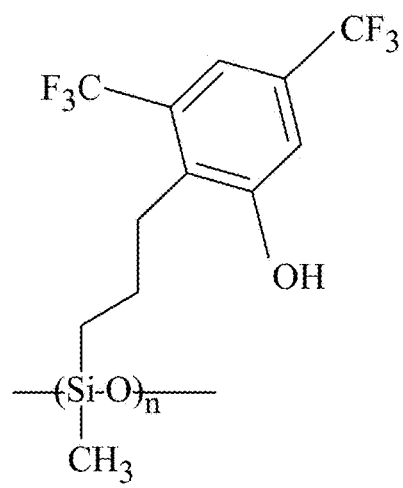
FIG. 2 is a schematic drawing of the repeat unit of DKAP, which is one example of a polymer suitable as an adsorbant coating for a SAW-based chemical detector.

For use in a chemical sensor, the adsorbent coating is then applied to the substrate surface. Numerous coatings, suitable for various applications, are known to those skilled in the art. Polymer coatings, among others, are often used. Typical polymer coatings include BSP3, poly(epichlorhydrin), ethyl cellulose, and DKAP. BSP3 is a fluorinated bisphenol-containing silicone polymer useful for the detection of organophosphorous compounds. DKAP, developed at Sandia National Laboratories, is similar to BSP3 but employs pendant 3,5-bis(trifluoromethyl)phenols to provide a stronger acid functionality. The DKAP repeat unit is shown in FIG. 2. To fabricate exemplary embodiments of our invention as described below, we manually applied several droplets of DKAP coating, in solution at a concentration of 0.0025 mg/mL, to each sensitized substrate.

As with any two-port band-pass filter, the SAW filter has parameters of insertion loss, input and output impedance, and stop-band loss. The input and output impedances are determined by the design of each IDT and by the coupling coefficient of the IDT metal fingers to the piezoelectric substrate.

The electrical input and output impedances of each IDT relate directly to the microwave scattering parameters (S-parameters) S11 and S22, respectively. It is advantageous to design each of the IDT impedances to be 50Ω at the center frequency of the SAW, because this provides optimum matching to most microwave test equipment as well as to most commercially available components that are likely to be used in a circuit design. We therefore chose 50Ω as the design impedance of the transducers in the embodiment described here.

Known principles are readily applied to design the IDT to attain any desired frequency over a broad range. The frequency f of the IDT is inversely proportional to its finger spacing and is related to the wavelength $\lambda$ of the surface acoustic wave by the familiar relation $f=v/\lambda$, where v is the acoustic velocity of the surface wave in the particular substrate material along a particular axis of propagation.

The insertion loss, bandwidth, and stop-band loss of the SAW device, however, are more difficult to design. The nature of the Rayleigh wave in a properly oriented crystal substrate is to be confined to a shallow surface channel of about the width of the transducer. This means that the wave emitted from an IDT will propagate equally in two directions, as a forward and a backward component. With this approach, half of the transmitted power will be lost on transmission and another similar proportion will be lost on interception at the output IDT. The insertion loss of such a design can never be better than about −12 dB.

To improve the insertion loss of the SAW device, reflectors can be added behind each IDT to create a resonating structure. Then, each successive pass of the wave between the reflectors will tend to couple some energy out. A resonator geometry has the added advantage that by increasing the effective number of passes of the acoustic wave through the detection zone where analyte is present, it can potentially increase the sensitivity of the detector.

Two general approaches are known in the art for creating a resonating acoustic cavity in a SAW device. The first approach is to create an acoustic Fabry-Perot resonator. This is done by adding multiple reflecting fingers made of metal or etched as grooves in the crystal surface. These are placed behind each IDT to reflect the backward travelling wave and resonantly couple it to the forward travelling wave. Thus, a resonant acoustic cavity is created by the pair of acoustic reflectors placed behind the respective IDTs.

The second approach to creating a resonant acoustic structure makes each finger pair of the IDT into its own reflector. That is, each finger pair of the IDT is designed in such a way that it transmits its wave, substantially, in only one direction. Similarly, any wave that such an IDT intercepts will either be absorbed or reflected, but not substantially transmitted. Such a transducer is referred to as a single phase uni-directional transducer (SPUDT). The exemplary embodiment of our invention described here uses a particular type of SPUDT design known in the art as a floating electrode uni-directional transducer (FEUDT) design.

Although the use of a Fabry-Perot resonator configuration has been tried by others in a SAW-based chemical detector, the embodiment to be described here is to the best of my knowledge the first SAW-based chemical detector in an SPUDT configuration.

Figure 3:
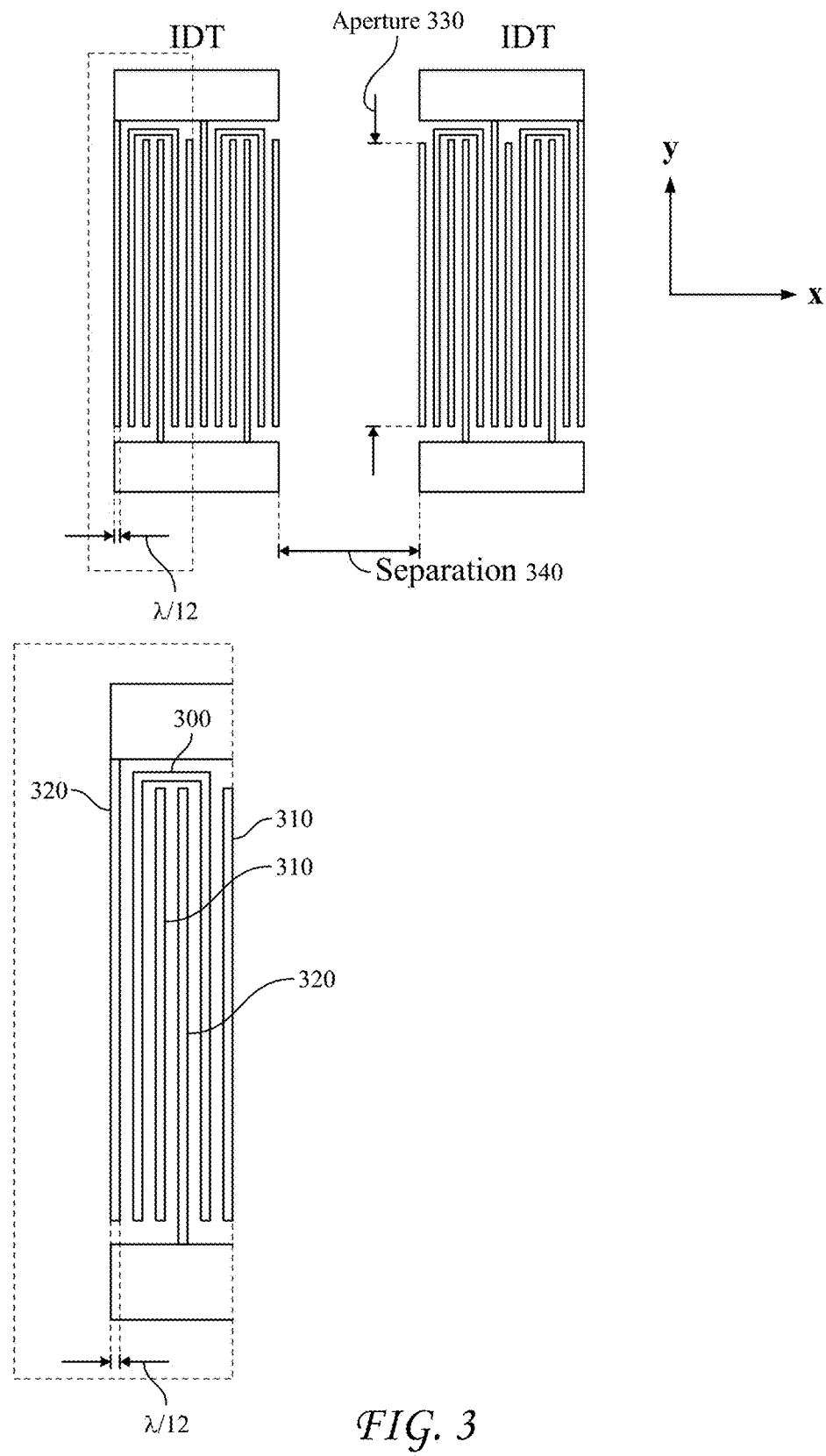
FIG. 3 provides a plan view of a floating-electrode unidirectional transducer (FEUDT) design for a resonant SAW device. The figure includes a detail with an expanded view of one finger-pair of an IDT.

FIG. 3 provides a plan view of an FEUDT design in which each IDT includes two finger-pairs. An expanded view of one finger-pair is shown in the detail to FIG. 3. As viewed in the figure, each finger-pair is a pattern consisting of six vertical projections and one shorting bar between two of the projections. A preferred width for the projections and the shorting bar is one-twelfth the resonant wavelength, because we found that this value makes the IDTs work best as unidirectional reflectors.

Each finger pair structure of the FEUDT IDT has three different elements. These are a pair of driver fingers, a pair of shorted fingers, and a pair of open or floating fingers. Additionally, each FEUDT IDT finger pair structure is replicated in one wavelength. Each FEUDT IDT then consists of 6 fingers with 6 spaces replicating in one wavelength. Making each finger and each space occupy a proportional distance in the finger pair structure means making each finger and each space one-twelfth of a wavelength.

As best seen in the detail to FIG. 3, each finger-pair of the IDT contains a pair 300 of shorted fingers that are connected by the shorting bar. Each finger-pair also contains a pair 310 of open fingers that are electrically floating, and a pair 320 of driver fingers that are respectively connected to the upper and lower bus bars.

Also indicated in FIG. 3 are the aperture 330 and the separation 340 between the respective IDTs.

Figure 4:
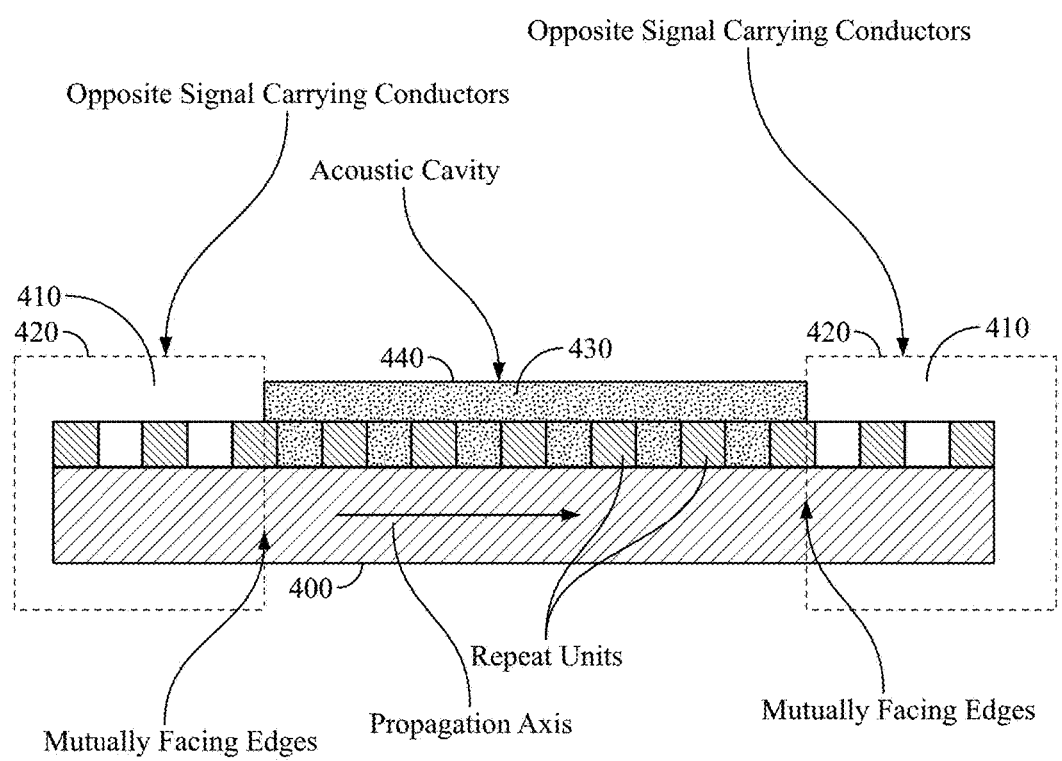
FIG. 4 is a conceptual cross-sectional view of a SAW device similar to the device of FIG. 3.

FIG. 4 is a conceptual cross-sectional view of a SAW device similar to the device of FIG. 3 as formed on a substrate 400. The view of FIG. 4 corresponds to a view along the y-axis as indicated in FIG. 3. With reference to FIG. 4, it will be seen that a few of the fingers 410 corresponding to the respective IDTs are shown in the figure. The bus bars are not shown. The portions corresponding to the respective IDTs are indicated by the boxes 420. In our currently preferred embodiment, the continuity of the mass loading due to the IDT finger pairs is continued all the way across the device by adding finger pattern 430, which covers the region between the IDTs with floating, i.e., unconnected, fingers that are exemplarily of similar dimensions and spacing to the fingers of the IDSs. We have found that pattern 430 helps to suppress undesired acoustic reflections from acoustic impedance discontinuities in the propagation path.

In some embodiments, each IDT includes a plurality of metal strips formed on the surface of the piezoelectric substrate and extending substantially perpendicularly to the propagation axis, said metal strips herein denominated fingers, that form a repeating pattern along said axis; and the apparatus includes a further plurality of fingers, herein denominated velocity-correcting fingers, that are formed in a repeating pattern along said propagation axis on at least a portion of said piezoelectric substrate that lies between said IDTs.

Also shown in FIG. 4 is the layer 440 of adsorbent material for sensitization. In our currently preferred embodiment, layer 440 is applied over pattern 430, so as to bury the fingers of pattern 430 and to fill the interstices between them. Comparative design studies indicated that for best performance, layer 440 should cover the full length of the propagation region between the IDTs, and that no portion of the device surface should be uncovered that constitutes a clear straight-line path from one IDT to the other IDT. We found that it is undesirable to cover the IDTs with adsorbant material, because that tends to increase insertion loss without increasing sensitivity.

As noted, our preferred design for the SAW device is an acoustically resonant design. This is desirable, among other reasons, because it helps to minimize the insertion loss, or power loss, from the output port of the device as referred to the input port (as these ports would be defined when viewing the device as a 2-port microwave network).

In comparative design studies, we found that the optimum type of resonator for the SAW device is an SPUDT resonator such as the FEUDT resonator described above. Comparative design studies also indicated that the detection signal-to-noise ratio tends to improve in proportion to the operating frequency, so for the greatest possible signal quality it is desirable to make the operating frequency of the device as high as possible. This will ultimately be limited by the fineness of the feature sizes that are manufacturable, which is dependent on the lithographic techniques used for device fabrication.

Comparative design studies also indicated that the separation between the IDTs is desirably made as large as possible to increase sensitivity, while still balancing the sensitivity gain against the increase in insertion loss caused by the separation. Although we tested devices with a separation of up to 400 wavelengths, we found that of those designs tested, the best performance was obtained with a separation of 200 wavelengths. As a general rule, we found that a separation in the range 100-400 wavelengths tends to provide the best performance.

Our studies also indicated that an IDT input impedance of 50Ω could be maintained by balancing the aperture dimension against the number of IDT finger-pairs. That is, the impedance tends to increase with the aperture size, and it also tends to increase with the number of finger-pairs. Hence, the target impedance of 50Ω could be maintained in the design by reducing the aperture size while compensating by adding more finger pairs.

We found that generally, the optimum aperture size is the smallest that is feasible in a given design, subject to the ability of the lithographic process to assure that the IDT fingers remain in phase with one another and subject to a limitation on the accumulated attenuation due to the lengthening IDT. Thus, an optimum IDT design has the narrowest aperture while still giving a 50Ω input impedance and the best attainable insertion loss.

The optimum number of finger-pairs in the IDT (as determined, e.g., by the requirement to maintain a 50Ω input impedance) is dependent on the operating frequency. At least for operation at a frequency of 1.8 GHz, we expect that the best performance will generally be obtained when there are 50-100 finger-pairs in the IDT.

As noted, we believe that the best performance will be obtained with the highest operating frequencies. We have tested devices up to 1.8 GHz, but we believe that devices can be made for operation at 2.4 GHz and still higher frequencies, and that performance will continue to improve with increasing frequency up to at least 2.4 GHz. We note in this regard that SAW-based chemical detectors of the prior art typically operate up to only about 500 MHz. However, we observed an improvement by a factor of four in sensitivity simply by increasing the frequency from 500 to 900 MHz, and by a further factor of three by going from 900 MHz to 1.8 GHz. Generally, fabrication techniques using electron-beam lithography will be needed to achieve the fine feature sizes necessary for operation at 900 MHz and greater frequencies.

Known approaches for measuring the change in mass loading due to analyte adsorption on the detector surface include frequency measurement and phase measurement. In frequency measurement, the SAW device is incorporated in a feedback oscillator, and changes in the oscillation frequency, relative to a reference oscillator, are measured. Our preferred approach, however, makes use of phase measurement, because we believe that better stability and noise performance can be obtained thereby.

Figure 5:
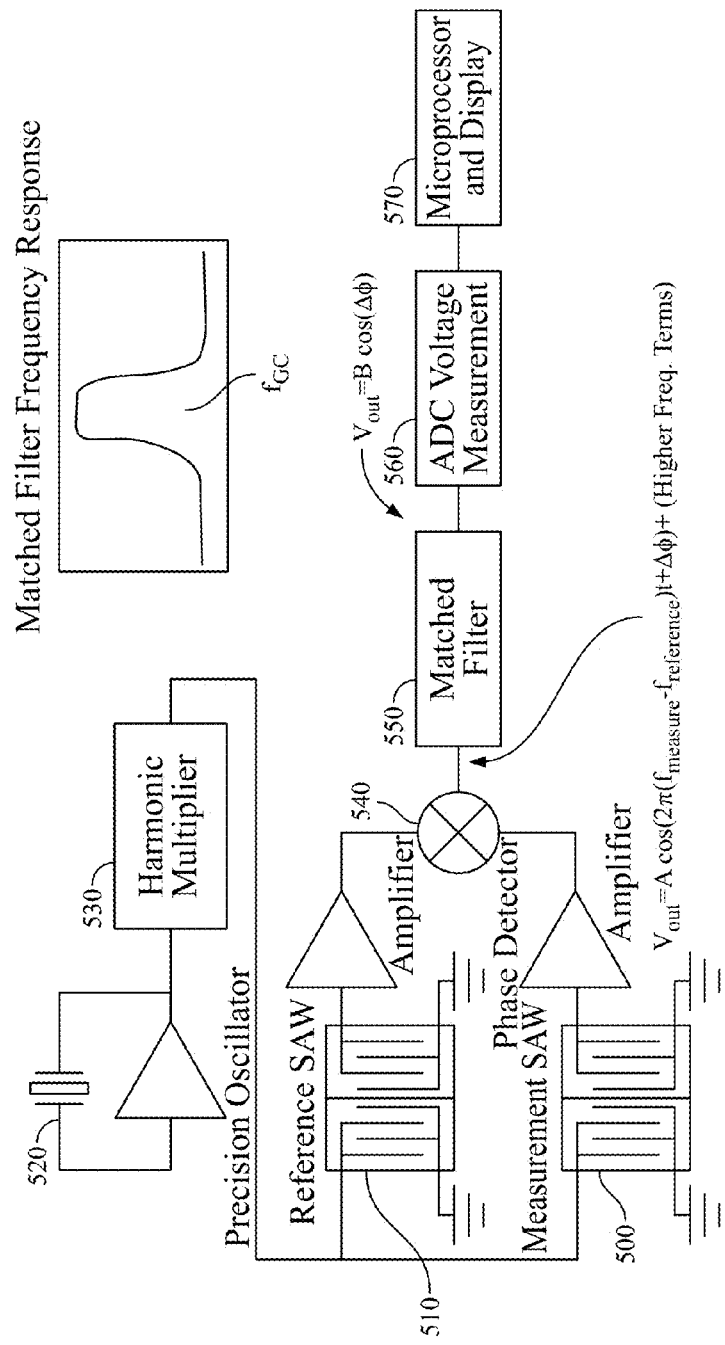
FIG. 5 is a schematic diagram illustrating one example of a measurement circuit according to an embodiment of the invention.

FIG. 5 is a schematic diagram illustrating our preferred measurement circuit at a conceptual level. The general features of our approach are known in the art, but we have added refinements to control phase noise throughout the detection electronics, and thereby to improve the noise performance of the circuit.

Turning to the figure, it will be seen that a measurement SAW device 500 and reference SAW device 510 are both driven by an oscillator circuit 520. We have found it advantageous to use a precision oscillator, i.e., an extremely stable oscillator with low phase noise. One example of such an oscillator is an oven-controlled crystal oscillator. However, oscillators of this type typically operate at frequencies that are substantially lower than the desired operating frequencies for the SAW devices. Accordingly, a harmonic multiplier 530 for use in stepping up the output frequency of the oscillator is also indicated in the figure. We note in this regard that although a frequency synthesizer could alternatively be used to step up the frequency, that would be more likely to increase the phase noise and degrade the measurement threshold of the chemical detector.

With further reference to the figure, it will be seen that the outputs of the measurement and reference SAW devices are directed to phase detector 540, which provides as output a time-varying voltage signal of, which to first order is, for example, proportional to $\cos(2\pi \cdot \Delta f \cdot t + \Delta \phi)$, where $\Delta f$ is the frequency difference between the measurement and reference SAW devices and $\Delta \phi$ is the phase difference between the acoustic signals received by the respective receiving IDTs.

The phase-detector output is directed to matched filter 550. A matched filter designed for use in a SAW or other resonator-based chemical detector is typically a bandpass filter with a very low center frequency. The high-pass portion of the filter characteristic will reject low-frequency drift components of the oscillators, the SAWs, or other component in the system. The low-pass portion will reject all of the mixing components of the phase detector as well as high-frequency noise from the amplifiers, mixer, reference oscillator, SAWs, and other spurious noise sources. The matched filter includes a template of the expected response signal obtained from the output of the phase detector. As is well-known in the art, such a template is correlated with the actual output response signal of the phase detector. Suitable matched filters can be implemented in analog or digital circuits, or in circuits that are analog-digital hybrids.

When the phase-measurement approach is implemented in conjunction with the combination of an oven-controlled crystal oscillator (or other extremely stable, low-phase-noise oscillator), a low-phase-noise harmonic multiplier, and a matched filter, a level of performance can be achieved that exceeds that of other measurement approaches in stability, noise performance, and measurement thresholds.

What is claimed is:

1. Apparatus for chemical detection comprising:
a pair of interdigitated transducers (IDTs) formed on a piezoelectric substrate; and
a layer of adsorptive material deposited on a surface of the piezoelectric substrate between the IDTs, wherein:
each IDT is conformed, and is dimensioned in relation to an operating frequency and an acoustic velocity of the piezoelectric substrate, so as to function as a single-phase uni-directional transducer (SPUDT) for surface-confined Rayleigh waves at the operating frequency, wherein the operating frequency is greater than 900 MHz, and is further conformed and dimensioned to have an input impedance at the operating frequency of about 50 ohms;
the piezoelectric substrate is a wafer of Y-propagation, Z-cut lithium niobate whereby acoustic waves launched into the piezoelectric substrate by at least one of the IDTs comprise surface-confined Rayleigh waves;
the pair of IDTs is spaced apart along a propagation axis and mutually aligned relative to said propagation axis so as to define an acoustic cavity that is resonant to surface-confined Rayleigh waves at the operating frequency, wherein a distance between each IDT of the pair of IDTs lies in the range from 100 wavelengths of the operating frequency to 400 wavelengths of the operating frequency;
each IDT comprises a plurality of metal strips formed on the surface of the piezoelectric substrate and extending substantially perpendicularly to the propagation axis, said metal strips herein denominated fingers, that form a repeating pattern of at least 50 but not more than 100 repeat units along said axis;
the apparatus comprises a further plurality of fingers, herein denominated velocity-correcting fingers, that are formed in a repeating pattern along said propagation axis on at least a portion of said piezoelectric substrate that lies between said IDTs;
the IDT fingers and the velocity-correcting fingers collectively form a single periodic pattern in which continuity of mass loading due to the IDT fingers is continued all the way across the piezoelectric substrate;
each IDT is conformed as a floating electrode uni-directional transducer (FEUDT); and
the IDTs have mutually facing edges, and the adsorptive layer covers the velocity-correcting fingers and extends from one said mutually facing edge to the other mutually facing edge without substantially encroaching on either of the IDTs.

2. The apparatus of claim 1, wherein
each repeat unit comprises:
two driver fingers that are electrically connected to opposite signal-carrying conductors;
two floating fingers that are individually electrically floating; and
two shorted fingers that are electrically shorted to each other.

3. The apparatus of claim 1, wherein:
the apparatus comprises at least one measurement sensor, at least one reference sensor, and an electronic circuit connected to the measurement and reference sensors;
the measurement sensor comprises the said IDT pair formed on the piezoelectric substrate and the said layer of adsorptive material deposited on the surface of the substrate between the IDTs;
the reference sensor comprises a further IDT pair formed on the piezoelectric substrate; and
the electronic circuit is conformed to detect phase differences between respective signals transmitted across the measurement and reference sensors.

4. The apparatus of claim 3, wherein:
each said IDT pair includes a transmitting IDT and a receiving IDT;
the electronic circuit includes a precision oscillator connected to the transmitting IDT of at least one said measurement sensor and at least one said reference sensor so as to drive acoustic oscillations of said transmitting IDTs;
the electronic circuit includes a phase detector connected to the receiving IDTs of said driven measurement and reference sensors;
the phase detector is conformed to provide an output signal that is indicative of said detected phase differences; and
the electronic circuit further comprises a matched filter connected to the output of the phase detector, wherein the matched filter is conformed to reject low-frequency drift components and high-frequency noise from the phase-detector output and to correlate an output response signal from the phase detector with a template representing an expected response signal.

5. The apparatus of claim 4, wherein the precision oscillator is an oven-controlled crystal oscillator.

6. The apparatus of claim 1, wherein the operating frequency is at least 1.8 GHz.

7. The apparatus of claim 1, wherein the pair of IDTs is separated by a distance selected to achieve a desired tradeoff between sensitivity and insertion loss.

8. Apparatus for chemical detection comprising at least one measurement sensor, at least one reference sensor, and an electronic circuit connected to the measurement and reference sensors, wherein:
the measurement sensor comprises a pair of interdigitated transducers (IDTs), consisting of a transmitting and a receiving IDT, formed on a piezoelectric substrate and spaced apart along a propagation axis and mutually aligned relative to said axis so as to define an acoustic cavity that is resonant to surface-confined Rayleigh waves at an operating frequency, wherein the operating frequency is greater than 900 MHz;
the piezoelectric substrate is a wafer of Y-propagation, Z-cut lithium niobate whereby surface-confined Rayleigh waves are launched into the piezoelectric substrate by at least one of the IDTs;
the measurement sensor further comprises a layer of adsorptive material deposited on a surface of the substrate between the IDTs;
the reference sensor comprises a further pair of IDTs, consisting of a transmitting and a receiving IDT, formed on a piezoelectric substrate and spaced apart along a propagation axis and mutually aligned relative to said axis so as to define an acoustic cavity that is resonant to surface acoustic waves (SAWs) at the operating frequency;

each IDT of said measurement and reference sensors is conformed, and is dimensioned in relation to the operating frequency and an acoustic velocity of the piezoelectric substrate, so as to function as a floating electrode uni-directional transducer (FEUDT) for surface-confined Rayleigh waves;

the FEUDT conformation of each IDT includes a repeating pattern of at least 50 but not more than 100 repeat units, each repeat unit comprises a plurality of metal strips, herein denominated fingers, that project substantially perpendicularly to the propagation axis; and each repeat unit comprises two driver fingers that are electrically connected to opposite signal-carrying conductors, two floating fingers that are individually electrically floating, and two shorted fingers that are electrically shorted to each other;

each of said measurement and reference sensors comprises a further plurality of fingers, herein denominated velocity-correcting fingers, that are formed in a repeating pattern along said propagation axis on a portion of the respective substrate surface that lies between the IDTs of the respective IDT pair so as to form, continuously with the IDT fingers, a single periodic pattern in which continuity of mass loading due to the IDT fingers is continued all the way across the piezoelectric substrate;

the adsorptive layer of the measurement sensor covers the velocity-correcting fingers and extends from an edge of one IDT of the pertinent IDT pair to an edge of the other IDT of said pair without substantially encroaching on either of said IDTs;

the electronic circuit includes a temperature controlled precision oscillator connected to the transmitting IDT of the measurement sensor and to the transmitting IDT of the reference sensor so as to drive acoustic oscillations of said transmitting IDTs;

the electronic circuit includes a phase detector connected to the receiving IDTs of the measurement and reference sensors, wherein the phase detector is conformed to provide an output signal that is indicative of phase differences between respective acoustic signals transmitted across the IDT pairs of the measurement and reference sensors;

the electronic circuit further comprises a matched filter connected to the output of the phase detector, wherein the matched filter is conformed to reject low-frequency drift components and high-frequency noise from the phase-detector output and to correlate an output response signal from the phase detector with a template representing an expected response signal;

each of the IDTs has an input impedance of about 50 ohms; and the pair of IDTs is separated by a distance of at least 100 wavelengths but is not more than 400 wavelengths of the surface-confined Rayleigh waves at the operating frequency.

* * * * *